United States Patent [19]

Nicolau et al.

[11] Patent Number: 5,332,710

[45] Date of Patent: Jul. 26, 1994

[54] VINYL ACETATE CATALYST PREPARATION METHOD

[75] Inventors: Ioan Nicolau; Philip M. Colling; Leland R. Johnson, all of Corpus Christi, Tex.

[73] Assignee: Hoechst Celanese Corporation, Somerville, N.J.

[21] Appl. No.: 961,738

[22] Filed: Oct. 14, 1992

[51] Int. Cl.$^5$ .................... B01J 37/03; B01J 21/08; B01J 23/44; B01J 23/52

[52] U.S. Cl. .................... 502/243; 502/330; 502/439; 502/300; 502/240

[58] Field of Search ............ 502/330, 243, 170, 439, 502/300, 240

[56] References Cited

U.S. PATENT DOCUMENTS

| | | | |
|---|---|---|---|
| 3,743,607 | 7/1973 | Sennewald et al. | 502/170 |
| 3,775,342 | 11/1973 | Kronig et al. | 502/170 |
| 3,822,308 | 7/1974 | Kronig et al. | 560/245 |
| 4,048,096 | 9/1977 | Bissot et al. | 502/170 |
| 4,087,622 | 5/1978 | Nakamura et al. | 502/170 X |
| 4,370,261 | 1/1983 | Wunder et al. | 502/328 |
| 4,902,823 | 2/1990 | Wunder et al. | 560/245 |
| 5,189,004 | 2/1993 | Bartley | 502/170 |

FOREIGN PATENT DOCUMENTS

| | | |
|---|---|---|
| 0464633A1 | 1/1992 | European Pat. Off. |
| 1521652 | 8/1978 | United Kingdom . |

OTHER PUBLICATIONS

Davidson, J. M. et al "Selectivity Problems and Kinetic Models in the Palladium Catalysed Oxidation of Ethene and Acetic Acid to Ethenyl Acetate. Related Reactions of Propene, 1-Butene and 1-Hexene." *Front. Chem. React. Eng.* [*Proc.-Int. Chem. React. Eng. Conf.*] vol. 1, 300–313. Wiley, N.Y. 1984.

*Primary Examiner*—Helen M. S. Sneed
*Assistant Examiner*—Douglas J. McGinty
*Attorney, Agent, or Firm*—Donald R. Cassady; Stuart D. Frenkel

[57] ABSTRACT

A method of preparing a catalyst particularly useful in the reaction of ethylene, oxygen and acetic acid in the vapor phase to form vinyl acetate comprises impregnating a porous support with water soluble salts of palladium and gold, fixing the palladium and gold on the support as water insoluble compounds by immersing the impregnated support in a reactive solution and tumbling the impregnated support in the reactive solution for at least ½ hour to begin precipitation of the insoluble compounds and completing precipitation of the insoluble compounds on the support and reducing the insoluble compounds to free palladium and gold. The catalysts prepared in this manner have been shown to provide improvement with respect to reduced selectivity to $CO_2$ during the vinyl acetate forming reaction.

19 Claims, No Drawings

VINYL ACETATE CATALYST PREPARATION METHOD

BACKGROUND OF THE INVENTION

1. Field of the Invention

The present invention relates to a novel method of producing a catalyst useful in the reaction of ethylene, oxygen and acetic acid in the vapor phase to form vinyl acetate. In particular, the present invention is directed to a novel method of forming a catalyst useful in the catalytic formation of vinyl acetate in which said catalyst comprises metallic palladium and gold deposited on a suitable porous support.

2. Description of the Prior Art

It is known in the an that vinyl acetate can be produced by reacting ethylene, oxygen and acetic acid in the gaseous phase and in the presence of a catalyst comprising palladium, gold and an alkali metal acetate supported on certain carrier materials such as silica. Generally, such catalyst systems exhibit a high activity. Unfortunately, results utilizing such palladium and gold catalysts have been inconsistent. This inconsistency appears to be based somewhat on the distribution pattern or profile of the catalyst components which are deposited on and in relation to the support. For example, when use is made of the known vinyl acetate catalyst systems comprising a porous support with palladium and gold, the metal components deposited at or about the support interiors or central regions do not contribute significantly to the reaction mechanism, since the reactants are not readily able to diffuse into the central or inner regions of the porous network of the catalyst. Hence, the reaction occurs substantially only at the outermost or surface regions of the catalyst. The catalyst components in the interior regions of the support do not largely contribute to the reaction scheme, resulting in a reduction in catalytic efficiency per unit weight of the catalyst components. Furthermore, the use of a highly active catalyst at times gives rise to side reactions and, therefore, leads to a reduced selectivity to vinyl acetate.

Various patents have been granted based on the desire to more evenly distribute and anchor the gold and palladium catalytic components within a narrow band on the support surface to provide a vinyl acetate catalyst having high yield, good selectivity and long life. Examples of such patents include U.S. Pat. Nos. 4,087,622; 4,048,096; 3,822,308; 3,775,342 and British Patent 1,521,652.

The basic method of forming the vinyl acetate catalyst containing palladium and gold deposited on a catalyst support comprises ( 1) impregnating the support with aqueous solutions of water-soluble palladium and gold compounds, (2) precipitating water-insoluble palladium and gold compounds on the catalyst support by contacting the impregnated catalyst support with a solution of compounds capable of reacting with the water-soluble palladium and gold compounds to form the insoluble precious metal compounds (3) washing the treated catalyst with water to remove anions which are freed from the initially impregnated palladium and gold compounds during precipitation and (4) convening the water-insoluble palladium and gold compounds to the free metal by treatment with a reducing agent. A final treatment usually involves (5) impregnating the reduced catalyst with an aqueous alkali metal acetate solution and (6) drying the final catalyst product.

Prior an attempts to provide a uniform distribution of the palladium and gold metals on the support have involved some manipulation of the above mentioned steps and/or by using support materials having various specified pore dimensions.

SUMMARY OF THE INVENTION

It has now been found that particularly active supported catalysts containing palladium and gold useful for the production of vinyl esters from ethylene, lower carboxylic acids with 2-4 carbon atoms and oxygen in the gas phase at elevated temperature and at normal or elevated pressure can be obtained by manipulating step (2) of the process as described above. Typically, during the precipitation step (2), the impregnated catalyst support is impregnated with a solution of the reactive compound and then allowed to stand for over 16 hours to complete precipitation of the insoluble precious metal compounds. The present inventors have found that during this "fixing" stage, a non-homogenous concentration of the reactive or fixing solution was created particularly at the contact points of the individual supports. To overcome this problem, a useful catalyst is formed by (1) simultaneously or successively impregnating a catalyst support with aqueous solutions of palladium and gold salts such as sodium-palladium chloride and auric chloride, (2) fixing the precious metals on the support by precipitating water-insoluble palladium and gold compounds by immersion of the impregnated supports in a reactive basic solution such as aqueous sodium hydroxide which reacts to form hydroxides of palladium and gold on the support surface, (3) washing with water to remove the chloride ion (or other artion), and (4) reducing the precious metal hydroxides to free palladium and gold, wherein the improvement comprises during fixing step (2) rotating the impregnated catalyst supports while such impregnated supports are immersed in the reaction solution at least during the initial precipitation period and prior to letting the treated catalyst stand for an extended period of time to continue the precipitation of the water-insoluble palladium and gold compounds. It has been found that rotating the impregnated supports while immersed in the reactive solution yields catalysts in which the precipitated support metals are more evenly distributed in a narrow band on the support surface. In this invention, rotation of the treated supports in the reaction or fixing solution is synonymous with tumbling, mixing, agitating, etc. What has been found is that catalyst activity with respect to the formation of vinyl esters such as vinyl acetate by the process of reacting ethylene, lower carboxylic acid and oxygen in the gas phase can be maintained and that the side reaction relative to the formation of carbon dioxide is substantially reduced when the catalysts are formed by the method described.

DETAILED DESCRIPTION OF THE INVENTION

In the preparation of the improved catalyst of the present invention, a suitable catalyst support is first impregnated with an aqueous solution containing water-soluble palladium and gold compounds. Separate solutions of palladium and gold compounds could also be used successively, but it is less convenient to proceed in that fashion. Palladium (II) chloride, sodium palladium (II) chloride, and palladium (It) nitrate are examples of suitable water-soluble palladium compounds, whereas auric (HI) chloride or tetrahaloauric (III) acid and the alkali metal salts thereof can be used as the water-soluble gold compounds. The generally available tetrachloroauric (III) acid and sodium palladium (II) chloride are preferred because of their relatively high water solubility. Typically, the quantity of these compounds employed is such as to provide 1 to 10 grams of palladium and 0.5 to 5 grams of gold per liter of finished catalyst. Accordingly, the mount of gold present in the catalyst will be from about 10 to about 70% of the mount of palladium. The mount of gold and palladium contained on the support has not been found to be critical to the method of preparation as catalysts formed by the rotation-immersion method of this invention with varied mounts of each precious metal have yielded similar improved results during the formation of vinyl acetate. Thus, catalysts containing even higher or lower amounts of the precious metals relative to that recited above could be useful in the formation of vinyl acetate by reaction of ethylene, oxygen and acetic acid in the vapor phase as long as the catalyst is formed by the novel method set forth herein. The volume of solution used for impregnating the support with the precious metals is important. For effective deposition, the volume of the impregnating solution should be from 95 to 100% of the absorptive capacity of the catalyst support and preferably it should be 98–99%.

The support material for the catalyst according to the present invention can be of any diverse geometrical shape. For example, the support can be shaped as spheres, tablets or cylinders. The geometrical dimensions of the support material can, in general, be in the range of 1–8 mm. A most suitable geometrical shape is, in particular, the spherical shape, for example, spheres with diameters in the range of 4–8 mm.

The specific surface area of the support material can vary within wide limits. For example, support materials which have an inner surface area of 50–300 m$^2$/g and especially 100–200 m$^2$/g (measured according to BET) are suitable.

Examples of support materials which can be used include silica, aluminum oxide, aluminum silicates or spinels. Silica is the preferred support material.

After impregnation of the support with the water soluble palladium and gold compounds, the impregnated supports can be dried or the fixing of the palladium and gold compounds can be accomplished while the support is still wet with the impregnating solution. The fixing solution is one which comprises an alkaline solution, for example, an aqueous solution which contains alkali metal hydroxides, alkali metal bicarbonates and/or alkali metal carbonates, alkali metal silicates, alkali metal borates, and hydrazine. It is particularly preferred to use aqueous solutions of sodium hydroxide or potassium hydroxide. The mount of the alkaline solution which should be utilized is important so as to ensure that all of the palladium and gold water soluble compounds are fixed or, in other words, precipitated in the form of water insoluble compounds. To ensure suitable fixing, it is useful to provide an amount of fixing solution such that the amount of alkali metal present is approximately 1–2 times the mount of total anion present in the water soluble precious metal salts. Preferably, ratios of alkali metal to anion range from about 1.6 to 1.2:1 molar. It is also important in the fixing stage, that the volume of fixing solution be such to immerse at least up to 50% of the surface area of the impregnated supports, preferably at least 75% of the surface area and most preferably a sufficient amount to wholly immerse the impregnated supports in the fixing solution prior to rotation or tumbling therein. Thus, the volume of fixing solution should equal about 50 to 500% of the volume of the impregnated supports. More preferably, an excess of fixing solution is used, e.g., 50 to 200 vol. % relative to the volume of the impregnated support.

By treatment with the alkaline solution, the precious metal salts are converted to water insoluble compounds believed to be hydroxides and/or oxides, at least in the case where the alkaline solution is a solution of sodium hydroxide or potassium hydroxide.

Previous to the present invention, the alkaline fixing solution was simply poured onto the impregnated supports and the treated supports were allowed to stand for up to 24 hours or more during the precipitation. It has now been found that catalyst activity such as for the formation of vinyl acetate can be maintained and that the side reaction relative to the formation of carbon dioxide can be substantially reduced if during the fixing stage, the impregnated supports are immersed in the alkaline solution and tumbled or rotated therein during the initial stages of precipitation of the water insoluble precious metal compounds such as to the oxides or hydroxides. The rotation or tumbling of the supports in the alkaline fixing solution should proceed for at least about 0.5 hour upon initial treatment and preferably for at least one hour. Rotation-immersion treatment can last as long as up to 4 hours. The treated supports may be allowed to stand in the fixing solution to ensure that complete precipitation of the water insoluble precious metal compounds takes place.

Any type of rotation, tumbling, or equivalent equipment which will keep the support in motion can be used as the exact apparatus utilized is not critical. What may be critical, however, is the extent of the motion. Thus, the motion should be sufficient so that all surfaces of the impregnated supports are evenly contacted with the alkaline fixing solution. The motion should not be so harsh that actual abrasion of the insoluble precious metal compounds takes place such that the insoluble compounds are abraded off the support surface. Generally, the extent of rotation should be about 1 to 10 rpm and possibly even higher depending upon the exact support utilized and the amount of precious metal to be deposited on the support. The rpm to be used is variable and may also depend upon the apparatus utilized, the size and shape of the support, the type of support, metal loadings, etc., but should fall within the guidelines expressed above. While a small mount of abrasion may take place, it is not to be such that the insoluble compounds are actually abraded off the support surface to an unacceptable degree.

Subsequent to the fixing and precipitation step, the supports are washed such as with distilled water so as to remove the anions, such as the chlorides, which are still contained on the support and freed from the initial impregnating solution. Washing is continued until all of the unions are removed from the support. No more than about 1,000 ppm of union should remain on the catalyst To ensure substantially complete removal of the unions such as chloride ion from the catalyst, the wash effluent can be tested with silver nitrate. The catalyst is then dried at temperatures not to exceed about 150° C. under an inert atmosphere such as a continuous nitrogen or air flow.

The fixed and washed material is then treated with a reducing agent in order to convert the precious metal salts and compounds which are present into the metallic form. The reduction can be carried out in the liquid phase, for example, with aqueous hydrazine hydrate, or in the gas phase, for example, with hydrogen or hydrocarbons, for example, ethylene. If the reduction is carried out with a solution of hydrazine hydrate, the reaction is preferably carded out at normal temperature. When the reduction is carded out in the gas phase, it can be advantageous to carry out the reaction at elevated temperature, for example, at 100°-200° C. in the case of reduction with ethylene. The reducing agent is appropriately employed in excess so that it is certain that all of the precious metal salts and compounds are converted into the metallic form.

Depending on the use for which the catalyst prepared in this way is intended, the latter can also be provided with customary additives. Thus, for example, additions of alkali metal acetates are advantageous when the catalyst is to be used for the preparation of unsaturated esters from olefins, oxygen and organic acids. In this case, for example, the catalyst can, for this purpose, be impregnated with an aqueous solution of potassium acetate and then dried.

The catalysts according to the invention can be used with particular advantage in the preparation of vinyl acetate from ethylene, oxygen and acetic acid in the gas phase. For this purpose, those catalysts according to the invention which contain silica as the support material and additives of alkali metal acetates are particularly suitable. In the above mentioned preparation of vinyl acetate, such catalyst are also distinguished by high activity and selectivity and by long life.

EXAMPLES 1-3

The catalysts of Examples 1-3 were prepared in accordance with the method of the present invention. For each example, silica catalyst supports provided by Sud Chemie having a spherical shape and a diameter as shown were utilized. Except as otherwise provided, the supports were impregnated with an aqueous solution containing sodium palladium chloride and sodium tetrachloroaurate in the concentrations shown unless otherwise indicated. 250 ml of the impregnated supports were placed in a round bottom flask containing 300 ml of an aqueous solution of sodium hydroxide. The amount of sodium hydroxide used corresponded to 120% of the stoichiometric equivalent needed to covert the precious metal salts to their hydroxides. The flask was immediately rotated in a roto-evaporator Without vacuum) at approximately 5 rpm and rotation continued for 2.5 hours. After 2.5 hours, the rotation was stopped and the alkaline treated supports may have been allowed to stand for an additional time as shown to insure maximum precipitation of the precious metal salts as the insoluble hydroxides. The flask was drained and the alkaline treated material was washed with distilled water to remove the chloride ions. The water flow rate was about 200 cc per minute for approximately 5 hours. The catalyst was dried at a temperature of 150° C. under a continuous nitrogen flow. The dried catalysts were reduced with ethylene at a temperature of 150° C. The reducing gas contained 5% ethylene in nitrogen and was passed over the catalysts for 5 hours at atmospheric pressure. The reduced catalyst was impregnated with an aqueous solution containing 10 grams of potassium acetate at a solution volume equal to the support absorbtivity. The catalysts were dried at a temperature no greater than 150° C.

CONTROL EXAMPLES A-F

Control Examples A-C were prepared by the method of U.S. Pat. No. 4,048,096 using the metal loadings, volumes, and concentrations provided in Table 1.

Control Examples D-F were prepared by the method of U.S. Pat. No. 3,775,342 using the metal loadings, volumes, and concentrations provided in Table 1.

TABLE 1

| Example. | Support Size Dia. mm. | Pd g/l | Au g/l | Tumbling Time hr. | Total Fix Time hr. | Shell Thickness | Shell Depth mm. | Std. Dev.[1] Shell Depth mm. | Vol. Fixing Sol. ml |
|---|---|---|---|---|---|---|---|---|---|
| EXAMPLES 1-3 | | | | | | | | | |
| 1. | 5.7367 | 3.3 | 1.5 | 2.5 | 2.5 | 2.70% dia. | 0.1549 | 0.0388 | 300 |
| 2. | 7.5050 | 5.0 | 2.27 | 2.5 | 2.5 | 2.58% dia. | 0.1936 | 0.0279 | 300 |
| 3. | 7.6092 | 6.6 | 3.0[3] | 2.5 | 18.5 | 2.60% dia. | 0.1980 | 0.0161 | 300 |
| CONTROL EXAMPLES A-F | | | | | | | | | |
| A. | 5.6650 | 3.3 | 1.5 | none | 16.75 | 3.617% dia. | 0.2049 | 0.0582 | 134 |
| B. | 7.6108 | 5.0 | 2.27 | none | 20.0 | 2.927% dia. | 0.2228 | 0.0332 | 134 |
| C. | 7.5958 | 6.6 | 3.0 | none | 17.0 | 2.933% dia. | 0.2228 | 0.0429 | 132 |
| D. | 5.7217 | 3.3 | 1.5 | none | 19.5 | 4.92% dia. | 0.2816 | 0.0490 | N.A.[2] |
| E. | 7.5317 | 5.0 | 2.27 | none | 19.5 | 5.75% dia. | 0.4330 | 0.0596 | N.A. |
| F. | 7.4733 | 6.6 | 3.0 | none | 19.0 | 6.54% dia. | 0.4884 | 0.0663 | N.A. |

[1]Standard Deviation
[2]Not applicable
[3]HAuCl4

What is claimed is:

1. In a method of preparing a catalyst composed of a porous support containing thereon precious metals which comprises impregnating said support with water soluble compounds of said precious metals, converting said water soluble precious metal compounds to water insoluble precious metal compounds by immersing said impregnated support in a fixing solution containing a compound reactive with said water soluble compounds to precipitate on said support said water insoluble precious metal compounds, washing said support, and reducing said water insoluble precious metal compounds with a reducing gas to form free precious metals on said support, the improvement which comprises tumbling said impregnated support by rotation at from about 1 to about 10 rpm at least 0.5 hour while said impregnated support is immersed in said fixing solution, thereby completing precipitation of said water insoluble compounds.

2. The method of claim 1 wherein said precious metals comprise a mixture of palladium and gold.

3. The method of claim 2 wherein said gold is present in an amount of 10 to 70% by weight of the amount of palladium.

4. The method of claim 2 wherein said support is tumbled in said fixing solution for at least about one hour.

5. The method of claim 1 wherein said reactive compound is an alkaline compound.

6. The method of claim 5 wherein said alkaline compound comprises potassium or sodium hydroxide.

7. The method of claim 5 wherein said alkaline compound is present in a molar excess relative to the amount required to convert all of said water soluble precious metal compounds to said precious metal water insoluble compounds.

8. The method of claim 5 wherein said water soluble precious metal compounds are salts and said alkaline compound is present in an amount such that the molar ratio of alkali metal of said alkaline compound to anion from said salt is from about 1.2:1 to 1.6:1.

9. The method of claim 7 wherein said fixing solution containing said alkaline compound is present in an amount to immerse at least 50% of the volume of said support.

10. The method of claim 9 wherein said fixing solution is present in an amount to immerse at least 75% of the volume of said support.

11. The method of claim 9 wherein the volume of said reactive solution is from about 50 to 500% of the volume of the impregnated support.

12. The method of claim 11 further including impregnating said reduced catalyst with an aqueous alkali metal acetate solution and drying said catalyst.

13. The method of claim 11 wherein said water insoluble precious metal compounds are reduced to free precious metals by contacting said treated support with a hydrocarbon gas.

14. The method of claim 13 wherein said hydrocarbon gas is ethylene.

15. The method of claim 1 wherein said porous support is silica.

16. The method of claim 2 wherein said porous support is silica.

17. In a method of preparing a catalyst composed of a porous support containing thereon a mixture of palladium and gold which comprises impregnating said support with water soluble salts of said palladium and gold, converting said salts to insoluble palladium and glod hydroxides by immersing said impregnated support in an aqueous sodium or potassium hydroxide solution to precipitate said hydroxides, washing said supports to remove freed anions from said salts and reducing said hydroxides with a reducing gas to form free palladium and gold on said support, the improvement which comprises tumbling said support therein by rotation at about 1 to about 10 rpm for at least 0.5 hour while said impregnated support is immersed in said aqueous sodium or potassium hydroxide solution, to complete precipitation of said hydroxides.

18. The method of claim 17 wherein the volume of said aqueous sodium or potassium hydroxide solution is from about 50 to 500% of the volume of the impregnated support.

19. In a method of preparing a catalyst composed of a porous support containing thereon a mixture of palladium and gold which comprises impregnating said support with water soluble chloride salts of said palladium and gold, converting said salts to water insoluble palladium and gold compounds by immersing said impregnated support in a solution containing an alkaline compound reactive with said salts to precipitate on said support said water insoluble compounds of said palladium and gold, washing said support to remove freed chloride ions and reducing said water insoluble compounds with a reducing gas to form free palladium and gold on said support, the improvement which comprises tumbling said support therein by rotation at about 1 to about 10 rmp for at least 0.5 hour while said impregnated support is immersed in said reactive solution, the volume of said reactive solution being about 50 to 500% the volume of said support and the alkaline compound being present in an amount such that the molar ratio of alkali metal of said alkaline compound to chloride anion of said salt equals from about 1.2:1 to 1.6:1, to complete precipitation of said water insoluble compounds.

* * * * *

UNITED STATES PATENT AND TRADEMARK OFFICE
CERTIFICATE OF CORRECTION

PATENT NO. : 5,332,710
DATED : July 26, 1994
INVENTOR(S) : Nicolau, et. al.

It is certified that error appears in the above-indentified patent and that said Letters Patent is hereby corrected as shown below:

Column 1, line 17, "an" should read "art".
Column 1, line 65, "convening" should read "converting".
Column 2, line 3, "an" should read "art".

Column 2, line 35, "artion" should read "anion".
Column 2, line 68, "(It)" should read "(II)".
Column 3, line 2, "(HI)" should read "(III)".
Column 3, line 10, "mount" should read "amount".
Column 3, line 12, "mount" should read "amount" (first occurrence).
Column 3, line 12, "mount" should read "amount" (second occurrence).
Column 3, line 16, "mounts" should read "amounts".
Column 4, line 61, "unions" should read "anions".
Column 4, line 62, "union" should read "anion".
Column 4, line 63, "unions" should read "anions".
Column 5, line 9, "carded" should read "carried".
Column 5, line 10, "carded" should read "carried".
Column 5, line 67, "without" should read "(without".
Column 8, line 3, "glod" should read "gold".

UNITED STATES PATENT AND TRADEMARK OFFICE
CERTIFICATE OF CORRECTION

PATENT NO. : 5,332,710
DATED : July 26, 1994
INVENTOR(S) : Nicolau, et. al.

It is certified that error appears in the above-indentified patent and that said Letters Patent is hereby corrected as shown below:

Column 8, line 34, "rmp" should read --rpm--.

Signed and Sealed this

Twenty-fourth Day of January, 1995

Attest:

BRUCE LEHMAN

Attesting Officer     Commissioner of Patents and Trademarks